US005299567A

United States Patent [19]

Joye et al.

[11] Patent Number: 5,299,567

[45] Date of Patent: Apr. 5, 1994

[54] MINIMAL ELASTANCE, CLOSED-CIRCUIT UNDERWATER BREATHING APPARATUS

[75] Inventors: Donald D. Joye, Exton, Pa.; Neal A. Carlson, Germantown, Md.

[73] Assignee: The United States of America as represented by The Secretary of the Navy, Washington, D.C.

[21] Appl. No.: 953,155

[22] Filed: Sep. 29, 1992

[51] Int. Cl.[5] .................. A61M 16/00; A62B 7/04

[52] U.S. Cl. .................. 128/204.28; 128/204.26; 128/204.29; 128/205.13; 128/205.22

[58] Field of Search .................. 128/200.24, 200.29, 128/204.28, 204.29, 205.13, 205.14, 205.15, 205.16, 205.17, 205.22, 204.26

[56] References Cited

U.S. PATENT DOCUMENTS

| | | | |
|---|---|---|---|
| 3,837,337 | 9/1974 | LaViolette | 128/205.12 |
| 3,877,425 | 4/1975 | O'Neill | 128/205.17 X |
| 3,934,581 | 1/1976 | O'Neill | 128/205.17 |
| 4,440,166 | 4/1984 | Winkler et al. | 128/204.22 |
| 4,964,404 | 10/1990 | Stone | 128/204.22 |
| 5,195,516 | 3/1993 | Grimsey | 128/204.26 |

FOREIGN PATENT DOCUMENTS

| | | | |
|---|---|---|---|
| 1058391 | 7/1955 | Fed. Rep. of Germany | 128/205.16 |
| 215576 | 5/1924 | United Kingdom | 128/205.22 |
| 829646 | 3/1960 | United Kingdom | 128/204.29 |

OTHER PUBLICATIONS

Younes et al, Am. Physiol. Soc.; 0161-7567/87, pp. 2491-2499.

Van Liew, Undersea Biomed. Res.; vol. 14, No. 2, Mar. 1987, pp. 149-160.

Fishman, Handbook of Physiology-Am. Physiol. Soc.; 87, pp. 145-177.

Joye et al, Formulation of Elastic Loading . . . ; NMRI Nov. 1989.

*Primary Examiner*—Edgar S. Burr
*Assistant Examiner*—Eric P. Raciti
*Attorney, Agent, or Firm*—A. David Spevack; William C. Garvert

[57] ABSTRACT

This invention comprises a minimal elastance underwater breathing apparatus (UBA) in which the elastance component of UBA impedance is substantially eliminated by forcing the breathing bag to expand and contract in a horizontal plane with small vertical displacements and hence minimal elastance. The invention further includes a servo-mechanism operating with a microprocessor, 3-axis position sensor and rotatable joints which act to keep the breathing bag oriented horizontally no matter what the diver's position. The principles of the present invention may be adapted to existing UBA with redesign and additions.

7 Claims, 3 Drawing Sheets

MINIMAL ELASTANCE, CLOSED-CIRCUIT UNDERWATER BREATHING APPARATUS

BACKGROUND OF THE INVENTION

1. Field of the Invention

This invention relates to the field of underwater breathing apparatus (UBA), more specifically to self-contained, closed-circuit underwater breathing apparatus, which operates without need of air or breathing gas from an outside supply remote from the diver, and wherein carbon dioxide gas ($CO_2$) generated by a diver is constantly removed and oxygen ($O_2$) needed for metabolism is constantly supplied.

2. Description of the Prior Art

A closed-circuit UBA is a form of self-contained underwater breathing apparatus (SCUBA) in which a diver's breathing gas is recycled through a closed loop, adding oxygen and removing carbon dioxide gases as needed. The carbon dioxide gas is typically removed by chemical absorption. UBA typically comprise an oxygen supply bottle, a canister containing $CO_2$ absorbent, a breathing bag or flexible volume element, connecting hoses, a mouthpiece for the diver, and a diluent gas or inert gas bottle. Inert gases such as helium or helium/nitrogen mixtures are often used. Some UBA versions monitor $O_2$ electronically and add oxygen when inspired $O_2$ concentrations drop below desired levels. The only mechanical adjustments that can be made by a diver involve the degree of filling of the breathing bags. As ambient pressure changes, for example as the diver goes deeper or rises, the volume of gas within the breathing bag(s) contracts or expands respectively, and diluent gas may be added or dumped, either manually or automatically. Some UBA have a single breathing bag; others have one for the inhalation side and another for the exhalation side of the recirculating loop.

The closed-circuit breathing apparatus and its basic construction and principles of operation have been known for some time (U.S. Pat. No. 3,837,337 to LaViolette, 1974). Improvements to such equipment are always being made for the diving community, which includes military, commercial underwater construction and salvage, and sport divers. For example, improvements in the control of air or breathing gas flow within the apparatus are discussed in U.S. Pat. No. 4,440166 to Winkler, et al, (1984), wherein particularly with respect to emergency mechanical control system in the event that the electronics fails.

The large majority of patents in the art center around the two critical performance factors for UBA, namely $CO_2$ absorption and $O_2$ control. Almost none deal with improving or lessening the difficulty of breathing-particularly during arduous exercise or heavy work. Those that do deal only with the fluid mechanical flow resistance and not other sources of impedance or mechanical resistance to breathing arising from the elements in the UBA including tubing or hoses, canister, etc. In general, breathing resistance in a UBA can be significant for the diver; it can reduce his effectiveness or the duration of work capability, and may, more seriously, contribute to loss of consciousness.

The mechanical resistance to breathing on a UBA is complex, because the breathing is sinusoidal or periodic in nature and not a steady flow. In this kind of flow situation dynamic analyses must be employed, such as those common to the art and discussed in detail by R. Peslin and J. J. Fredberg, "Oscillation Mechanics in the Respiratory System, chap. 11 in *Handbook of Physiology: vol III, The Respiratory System*, A. P. Fishman (ed.), 1987, American Physiol. Soc., Bethesda, Md., and H. D. Van Liew, "The Electrical-Respiratory Analogy when Gas Density is High", Undersea Biomedical Research, vol. 14, no. 2 (1987) pp. 149-160. In a periodic flow, allowance must be made for additional resistances to the motion of the breathing gas. These resistances are termed elastance and inertance and they cause increased energy loss, because the diver must overcome them as well as the resistance due to flow to keep breathing. Inertial resistance or inertance arises from accelerations and decelerations in the gas flow and displaced water due to the periodic nature of the flow. This generally becomes important only at high frequencies that are generally much higher than human breathing patterns, even under sustained work loads. Inertance increases with depth due to the gas density increasing, but rarely contributes to impedance at the breathing frequencies normally used by a diver.

Elastic resistance or elastance arises from pressure changes as a result of flow entering a closed volume or pressure changes as volume changes (in submersed breathing bags for example). Because of the oscillatory or periodic nature of the flow, complex algebra must be used to describe the overall resistance to flow, which is termed the impedance. Therefore;

$$Z=R-(jE/\omega)+j\omega I \quad \text{Eqn. 1}$$

where Z is the impedance in units of pressure/flow rate, R is the resistance due purely to flow (the flow resistance) in the same units, E is the elastance in units of pressure/volume, I is the inertance in units of pressure/-flow acceleration, and $\omega$ is the radian frequency in units of reciprocal time. Eqn. 1 applies to a series arrangement of R, E and I, typical of UBA. Impedance is composed of a real part, the flow resistance, and an imaginary part, which is a combination of the inertance and the elastance. The magnitude of Z can be computed by;

$$|Z|=\sqrt{[R^2+(\omega I-E/\omega)^2]} \quad \text{Eqn. 2}$$

so that all three components of impedance contribute to overall energy loss in the flow system. The energy loss is reflected in the pressure drop required to cause flow.

The foregoing are terms of the art necessary to understand the present invention, but they do not constitute the invention.

Flow resistance is present at all times by virtue of the flow rate of gas being moved. The pressure drop required to cause flow at a given rate increases with flow rate in a complicated manner when flow resistance is present. Elastance contributes to the impedance at low frequencies which are generally in the range of a diver's breathing frequencies, whether the diver is at rest or working. It is therefore a major part of the impedance of the UBA. As breathing frequency increases the flow resistive part becomes increasingly more important and elastance increasingly less important factor in the pressure required to maintain flow.

Impedance in the UBA adds to the positive and negative respiratory pressures that a diver must generate to breathe. Impedance is generated by the elastance, inertance and resistance in the UBA. Resistance in UBA arises from breathing hoses, valves, changes in flow diameter, the canister and other similar obstructions in the flow path. Resistance is the fluid mechanical cost of moving the fluid at a given rate. The ratio of the pressure required to drive the flow and the volumetric flow rate is termed the flow resistance.

Elastance is the reciprocal of compliance in the system and is derived in UBA primarily from changes in volume of the breathing bag when immersed. If these changes in volume lead to a vertical expansion or contraction of the bag, pressure is altered by hydrostatic forces, wherein the pressure change (ΔP) is given by;

$$\Delta P = \rho g \Delta h \quad \text{Eqn. 3}$$

where Δh is the vertical displacement and ρ is the density of the ambient fluid, usually water or sea water, and g is the acceleration of gravity. The shape of the bag and its orientation in the water have an effect of the elastance. Reference is made to D. D. Joye, J. R. Clarke, N. A. Carlson and E. T. Flynn, "Formulation of Elastic Loading Parameters for Studies of Closed-Circuit Underwater Breathing Systems", NMRI Technical Report 89—89, Bethesda, Md., 1989 (report available from NTIS, Washington, D.C.). Elastance is inversely proportional to the cross-sectional area that is perpendicular to the vertical direction. If the volume change in the breathing bag had no vertical component, for example if the bag changed shape in a horizontal direction only, there would be no change in pressure due to volume change and hence no elastance (except for some possible hydrostatic change in an uneven bag fill). There are other contributions to elastance in a UBA, for example the volume of internal hoses and containers in the breathing loop, that have an additional, but much smaller, effect.

The force that moves the flow of breathing gas is respiratory pressure. Although the respiratory pressure imposed by UBA elastance can be relatively high at the low frequencies commonly encountered in a diver's breathing pattern, which is typically in the range 5-60 breaths/minute, particularly 10-40 bpm, there have been no efforts to either statically or dynamically reduce UBA elastic impedance to make it easier for the diver to breathe.

SUMMARY OF THE INVENTION

Accordingly, an object of this invention is to eliminate insofar as possible elastic impedance in UBA.

This and additional objects of the invention are accomplished by (a) designing the breathing bag so that volume changes are accomplished without substantial vertical component, and (b) a means of positioning the breathing bag such that (a) is accomplished regardless of the attitude or orientation of the diver.

BRIEF DESCRIPTION OF THE DRAWINGS

A more complete appreciation of the invention will be readily obtained by reference to the following Description of the Preferred Embodiments and the accompanying drawings The representation in the figure is diagrammatic and no attempt is made to indicate actual scales or precise ratios.

FIG. 1(*a*) is a detail of FIG. 1

DESCRIPTION OF THE PREFERRED EMBODIMENTS

Figure 1:
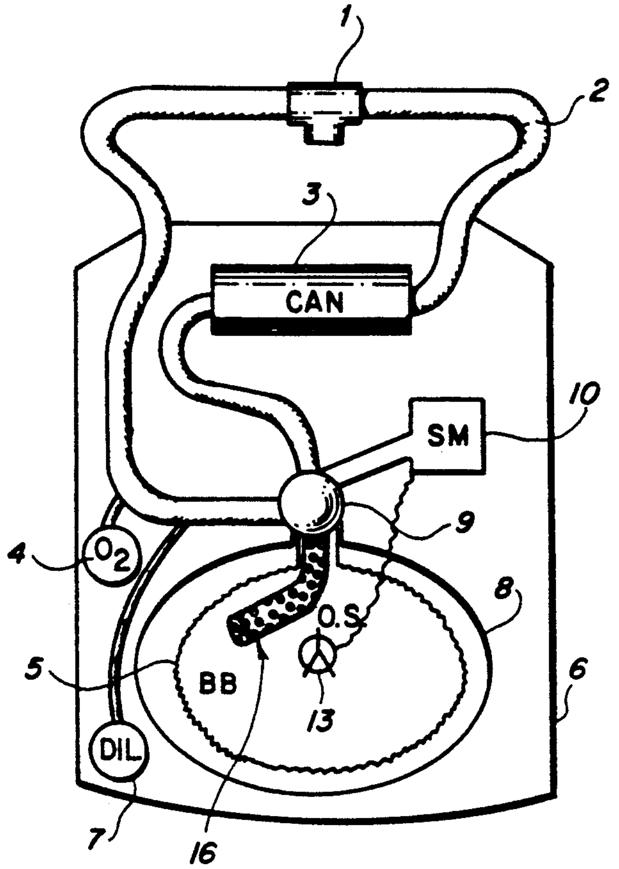
FIG. 1 shows the features of the present invention incorporated into an otherwise typical recirculating underwater breathing apparatus.
Figure 1A:
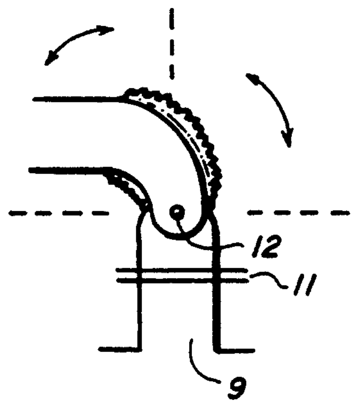
Figure 2B:
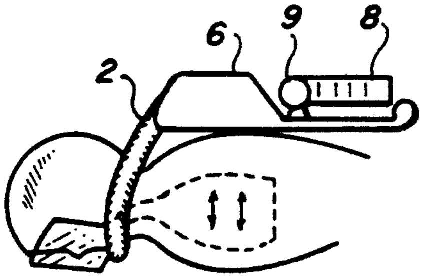
FIG. 2(*a–d*) shows various orientations of the UBA and diver with the breathing bag always in the horizontal position.
Figure 2C:
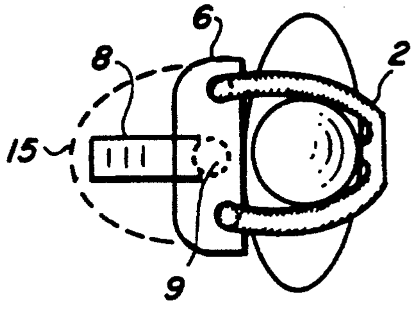
Figure 2A:
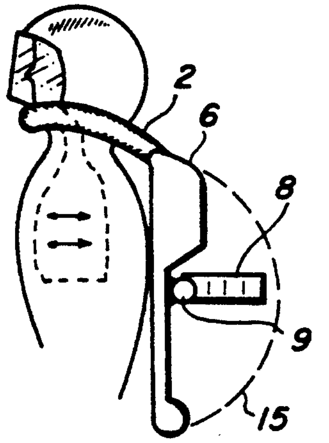
Figure 2D:
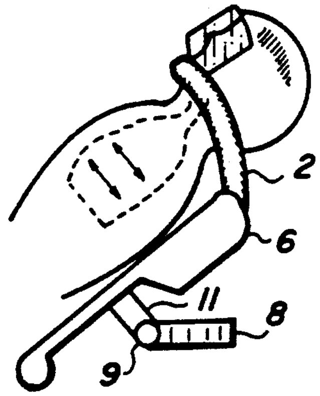

The invention comprises (a) a breathing bag adapted to change volume in a horizontal direction predominantly and (b) a means for positioning the breathing bag such that horizontal expansion continues to occur regardless of the diver's orientation or attitude in the water.

More particularly, in one embodiment, the breathing bag design is a flat bladder shape, constrained on the flat sides by a housing or container and oriented horizontally such that the flat sides are parallel to the horizon. The inlet/outlet opening is on the cylindrical or curved surface of the bag, and bag expansion and volume change can occur in a horizontal direction almost completely. Whatever vertical component may exist is minimized by having a large, flat horizontal surface to the bag, so that for a given tidal volume of breathing, for example, the bag moves a minimal distance vertically.

In another preferred design, the housing is the same, but the bag has a tubular, spiral shape. This bag expands and contracts in a horizontal plane defined by the upper and lower plates of the housing. One end of the breathing bag tube is closed and the other connected to a 90 degree rotatable joint which is connected to a completely (360 degree) rotatable collar. A servo-mechanism senses the position of the bag and adjusts the bag to keep it in a horizontal position, regardless of the orientation of the diver.

Having described the invention, the following examples are given to illustrate specific applications of the invention including the best mode now known to perform the invention. There may be other ways to do the basic tasks of the present invention, once the invention is known, thus these specific examples are not intended to limit the scope of the invention described in this application.

To keep the breathing bag horizontal in the water, its position in space must be sensed by a 3-axis position indicator located within or on the breathing bag housing of the UBA. Position indicators are more common to the aerospace art, particularly airplanes with pitch (up and down at the head), yaw (side-to-side) and roll axes and displays common in the cockpit. A position indicator adapted for use underwater is described here as an example: Three pressure transducers are placed in a horizontal plane on the breathing bag housing, and pitch, roll and yaw are determined by the different readings on these transducers. For example, the north transducer reads pressure A, the west transducer reads pressure B, and the east transducer reads pressure C. If A=B=C, the diver is horizontal (pressure is relative to a common point on the UBA, preferably in the center). If B>C and both greater than A, then the diver is pitched down at the head and rolling to the right. The degree to which this is true depends on the magnitude of the pressure signals. Many other combinations could be discussed, but the principle is clear. This provides a signal for corrective action to be taken by the servomechanism to right the breathing bag housing to the horizontal position.

The pressure transducers may be of any type current in the diving art, such as the metal diaphragm differential pressure cells manufactured by Validyne Engineering Corporation, Northridge, Calif., or a miniaturized piezoelectric device adapted for use underwater, or pressure transducers whose working principles can be adapted for underwater use. These transducers sense differential pressure by deflection of a diaphragm or stretching of a thin film of material, which changes the resistance or other electrical properties of the material; these in turn can be sensed as a voltage or current change. The microprocessor can be any adaptation of similar units nowadays commonly used in automobiles to monitor engine function and effect changes in the operating variables. The appropriate circuit design simply needs to be carried out and the unit programmed to obtain the desired functional performance. This is well within the skill of the present electronic art.

With reference to FIG. 1, basic elements of the UBA and features of the present invention are shown. The diver breathes on mouthpiece. [1]. Breathing gas circulates through hose [2]; arrows show direction of gas motion. The $CO_2$ from the diver's exhale gas is absorbed in canister [3], make-up oxygen is added by oxygen bottle [4] as needed. The breathing bag [5] provides a capacitance in the system. The UBA housing [6] is generally porous to water, so all the elements are in a water environment. Diluent gas bottle [7] for adjusting volume in the breathing bag is also shown.

With respect to the elements of the present invention, the breathing bag housing [8] has a disc or coin shape, circular in one plane and thin in the depth dimension. A preferred diameter is in the range 12–15 inches and thickness about 2–3 inches to provide enough volume (about 3–5 liters) for tidal volume excursions in the diver's breathing pattern. The breathing bag housing is moveable and rotatable through joint [9] and servomotor [10], which also contains a microprocessor or computer function. Anti-collapse structure shown as perforated tube [16] prevents total collapse of the bag. Other structures, such as wire grid works modeled after devices used to prevent tennis dome collapse or other gas bag collapse can be substituted. FIG. 1(*a*) shows a detail of one embodiment of a moveable and rotatable joint. Joint is rotatable 360 degrees through collar [11] and the breathing bag housing can be raised through 90 degrees through hinge pin [12].

Alternatively, it may be preferred to design this joint with a full 180 degree capability for easier positioning of the breathing bag housing when the diver is almost prone, facing up. In these cases, it would be desirable to have an extension capability in the tube that contains the rotatable collar, so that the UBA housing can be safely cleared. The alternative is to design the length of the tube such that the breathing bag housing clears the UBA for all 360 degrees. The joint may be a complex assembly of several single moveable joints rotating in one plane only, or may be a ball-type joint completely rotatable in all directions. The specifics of the joint design are within the skill of the art. Only typical examples are presented here. The position of the bag is sensed by a 3-axis orientation indicator [13], whose signal is sent to the servo-motor and control computer/microprocessor [10].

FIG. 2 shows how the breathing bag housing would look under different conditions of diver orientation. In FIG. 2(*a*) the diver and UBA are upright, and the breathing bag housing [8] is horizontal as shown. In FIG. 2(*b*) the diver and UBA are in the prone position, and the breathing bag housing [8] is close to the back of the diver. In FIG. 2(*c*) the diver and UBA are prone on the side, and the breathing bag will extend outward from the back as shown. In FIG. 2(*d*) the diver and UBA are semi-prone, facing up. The bag assumes the horizontal position shown, clearing the UBA housing. Alternatively, a protective, porous, rigid, second housing [15], illustrated in FIG. 2(*a*) and 2(*c*), can surround the bag movement area. The housing [15] can be any rigid, porus, protective structure such as wire grid etc. well known from similar structures in the art.

Figure 3:
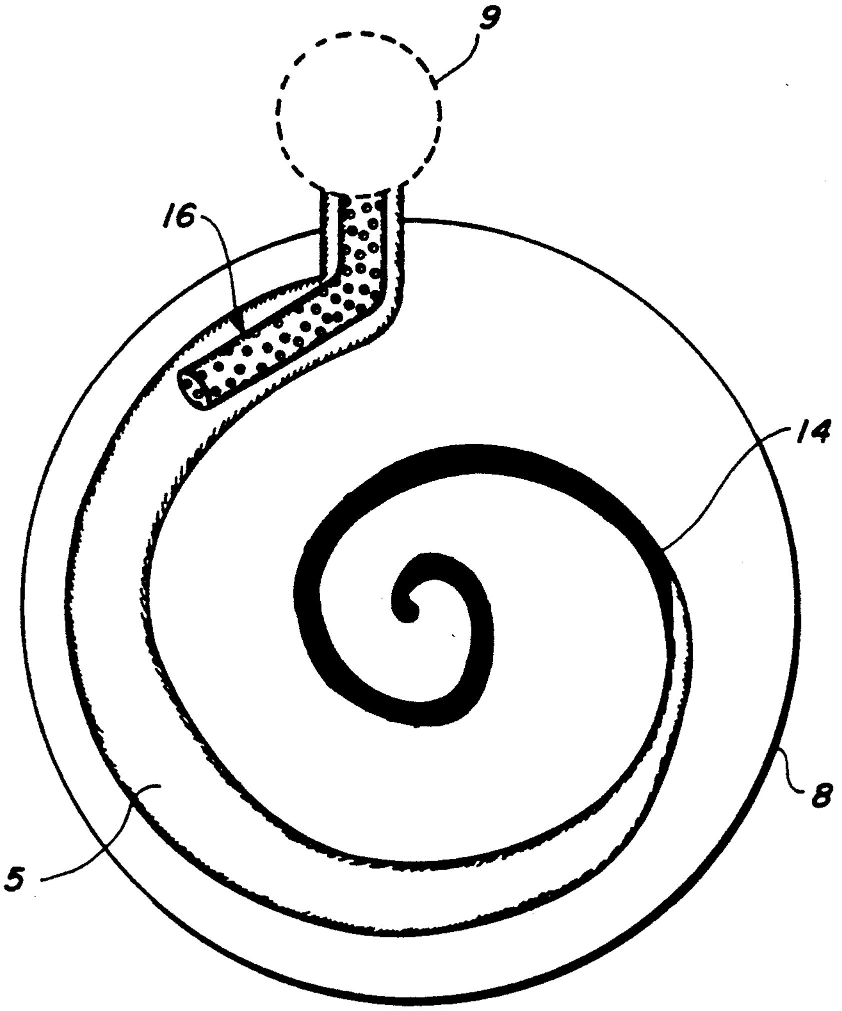
FIG. 3 shows an alternative breathing bag design for the present invention.

FIG. 3 shows a schematic of the spiral breathing bag [5] and housing [8]. The spiral bag needs a mechanism to keep one end collapsed, yet extensible. Collapsed part of the breathing bag [14] is shown in FIG. 3 also, for a volume of air that does not fill the complete volume of the tubular, spiral breathing bag. Keeping one end collapsed is accomplished by an axial flat-wire spring imbedded in the bag material, for example, but other ways known to the art may also be used. The spring must be of a stiffness to substantially retract the bag under zero pressure differential, yet allow expansion without much pressure differential. The pressure differential for expansion vs. the amount expansion is the elastic characteristic of the bag. This should be kept below about 2–3 inches of water for the purposes of this invention, preferably below 1 inch of water equivalent pressure.

When the bag of FIG. 3 inflates or deflates, it moves in a spiral path and expands horizontally. Thus the housing must be porous to allow movement of water therethrough and rigid to contain the ultimate expansion of the bag. As long as the housing or restrictive structure of the discs is kept horizontal, the elastance of this system is minimal. Horizontal placement is accomplished by the servomechanism and microprocessor adjusting the rotatable joints.

In an especially preferred embodiment, the bag is bladder-shaped, as shown in FIG. 1, and thin and circular like a short cylinder. Preferably, the bag has a mesh tube or other porous structure inserted inside to prevent collapse of the walls when evacuated. This function is provide in UBA's of the art in many similar ways. Thus, minimal elastance is produced from a large, flat surface kept in a horizontal orientation. Changes in volume of the bag due to a tidal breath, for example, result in a relatively small change in vertical dimension. We estimate this to be about 2–3 inches, typically, and preferably about 1 inch.

The breathing bag housing is rigid and porous and should not need any further protection. However, because it is moveable and protruding, a second housing may be desired. This housing should also be rigid and porous, but must be large enough to contain all possible configurations of the breathing bag housing. This adds a large bubble on the divers back which may limit access to narrow passageways, but will provide protection from snagging or bumping of the bag housing on foreign objects. One way the size of this second housing can be reduced is to give the rotatable joint [11] moveable as well as extensible capability. This is done by the joint being mounted on tracks and moved by another motor controlled by the microprocessor or computer. These and other variations are well within the current skill of the electronic and mechanical arts.

Obviously, many modifications and variations of the present invention are possible in light of the above teachings. It is therefore to be understood that, within the scope of the appended claims, the invention may be practiced otherwise than as specifically described.

What is claimed is:

1. A minimal elastance underwater breathing apparatus (UBA) adapted to recirculate breathing gas, absorb $CO_2$, add make-up oxygen, and provide capacitance through a breathing bag, comprising:

(a) a breathing bag with the capability of a large change in volume in a first direction without substantial change in a second direction perpendicular to the first direction said first direction being horizontal to the water surface and the second direction being a vertical component, and;

(b) a means for maintaining said breathing bag in a position so the large volume expansion is horizontal regardless of the spatial orientation of the diver.

2. The minimal elastance UBA of claim 1, wherein the bag shape is a tubular spiral wherein the large volume is caused by the spiral being adapted to fold, expand and contract in the first direction with breathing of a diver, along a spiral path constrained on top and bottom by a rigid, porous housing.

3. The minimal elastance UBA of claim 1, wherien the bag is a cylinder, the diameter of the cylinder being substantially greater than the height of the cylinder, the circular cross section of the cylinder is oriented in the first direction and the cylinder is adapted to fit in a porous housing of the same shape, and the bag contains an anti-collapse structure within said bag to prevent collapse of the bag on evacuation.

4. The minimal elastance UBA of claim 1, wherein said UBA additionally contains a second housing covering the space occupied by all possible positions taken by said breathing bag as it moves to maintain the first direction horizontal, said second housing being rigid and porous to protect said breathing bag housing from foreign objects and to permit water to move therethrough.

5. The minimal elastance UBA of claim 1, wherein the means for maintaining the first direction of said breathing bag in a horizontal position comprises a servomechanism, a microprocessor, a 3-axis position indicator, and a rotatable joint assembly, said position indicator is mounted on a housing surrounding and protecting said breathing bag, said position indicator senses the spatial position of said housing and sends an appropriate signal to said microprocessor, said microprocessor compares this signal with horizontal base level and controls said servomechanism to move said housing through actions taken through said joint assembly to bring said breathing bag into horizontal position.

6. The minimal elastance UBA of claim 5, wherein the means for maintaining the first direction horizontal is a set of tracks on the UBA housing.

7. In an underwater breathing apparatus (UBA) of the type adapted to recirculate breathing gas to a diver, absorb $CO_2$, add make-up oxygen and provide capacitance through a breathing bag, a method of substantially eliminating elastic component of impedance by (a) adapting said breathing bag to change volume without substantial vertical component and (b) maintaining said breathing bag in a horizontal position regardless of the orientation of the diver.

* * * * *